US010690685B2

(12) United States Patent
Mao et al.

(10) Patent No.: US 10,690,685 B2
(45) Date of Patent: Jun. 23, 2020

(54) MECHANOCHEMICAL PLATFORM AND SENSING METHODS USING DNA ORIGAMI NANOSTRUCTURES

(71) Applicants: KENT STATE UNIVERSITY, Kent, OH (US); KYOTO UNIVERSITY, Kyoto-shi, Kyoto (JP)

(72) Inventors: Hanbin Mao, Kent, OH (US); Deepak P. Koirala, Kent, OH (US); Hiroshi Sugiyama, Kyoto (JP); Masayuki Endo, Kyoto (JP)

(73) Assignee: KENT STATE UNIVERSITY, Kent, OH (US)

( * ) Notice: Subject to any disclaimer, the term of this patent is extended or adjusted under 35 U.S.C. 154(b) by 478 days.

(21) Appl. No.: 15/315,856

(22) PCT Filed: Jun. 5, 2015

(86) PCT No.: PCT/US2015/034396
§ 371 (c)(1),
(2) Date: Dec. 2, 2016

(87) PCT Pub. No.: WO2015/188053
PCT Pub. Date: Dec. 10, 2015

(65) Prior Publication Data
US 2017/0108517 A1    Apr. 20, 2017

Related U.S. Application Data

(60) Provisional application No. 62/008,529, filed on Jun. 6, 2014, provisional application No. 62/084,687, filed on Nov. 26, 2014.

(51) Int. Cl.
*G01N 33/74* (2006.01)
*B82Y 15/00* (2011.01)
(Continued)

(52) U.S. Cl.
CPC ............ *G01N 33/74* (2013.01); *B82Y 5/00* (2013.01); *B82Y 15/00* (2013.01); *C07H 21/02* (2013.01);
(Continued)

(58) Field of Classification Search
CPC .............. G01N 33/74; G01N 33/5308; G01N 33/54366; G01N 2333/49; B82Y 5/00;
(Continued)

(56) References Cited

U.S. PATENT DOCUMENTS

| 7,652,731 B2 | 1/2010 | Chien et al. |
| 2014/0066610 A1* | 3/2014 | Schaus ................. C12Q 1/6816 536/23.1 |

OTHER PUBLICATIONS

Kuzuya et al. (Methods 67 (2013) 250-255). (Year: 2013).*
(Continued)

*Primary Examiner* — Sally A Merkling
(74) *Attorney, Agent, or Firm* — Hudak, Shunk & Farine Co. LPA

(57) ABSTRACT

A biosensing platform capable of high throughput mechanochemical biosensing comprising a DNA origami nanostructure having a plurality of slots into which recognition elements are strategically placed and apparatus that senses a change in the origami nanostructure in response to the introduction of a target where the apparatus includes a signal transduction unit and signal sensor which exploits mechanical signals in a recognition element which signal includes one or more mechanical tension or mechanochemical rearrangement event. The nanostructure is preferably a 2-dimensional or 3-dimensional arrangement of tiles linked by locking elements, such as aptamers that will open in response to an event such as exposure to a drug molecule, DNA, RNA or protein target.

15 Claims, 5 Drawing Sheets

(51) Int. Cl.
  *C07H 21/02*   (2006.01)
  *C12Q 1/6825*  (2018.01)
  *B82Y 5/00*    (2011.01)
  *G01N 33/53*   (2006.01)
  *G01N 33/543*  (2006.01)
  *B82Y 40/00*   (2011.01)

(52) U.S. Cl.
  CPC ....... *C12Q 1/6825* (2013.01); *G01N 33/5308* (2013.01); *G01N 33/54366* (2013.01); *B82Y 40/00* (2013.01); *G01N 2333/49* (2013.01); *Y10S 977/832* (2013.01); *Y10S 977/88* (2013.01); *Y10S 977/924* (2013.01)

(58) Field of Classification Search
  CPC ...... B82Y 15/00; B82Y 40/00; C12Q 1/6825; C07H 21/02; Y10S 977/924; Y10S 977/88; Y10S 977/832
  See application file for complete search history.

(56) References Cited

OTHER PUBLICATIONS

Do et al. (Nano Lett. Sep. 12, 2012; 12(9)). (Year: 2012).*
Yangyuoru, M., et al., Single-Molecule Measurements of the Binding between Small Molecules and DNA Aptamers, Anal. Chem, 2012, vol. 84, pp. 5298-5303, American Chemical Society, ACS Publications.
Rinker, S., et al., Self-assembled DNA nanostructures for distance-dependent multivalent ligand-protein binding, Nature Nanotechnology, vol. 3, 2008, pp. 418-422, Macmillan Publishers Limited.
Zhao, Z, et al, Organizing DNA Origami Tiles into Larger Structures Using Preformed Scaffold Frames, Nano Lett, 2011, vol. 11, pp. 2997-3002, American Chemical Society, ACS Publications.

* cited by examiner

MECHANOCHEMICAL PLATFORM AND SENSING METHODS USING DNA ORIGAMI NANOSTRUCTURES

FIELD OF THE INVENTION

The invention relates generally to a biosensing platform and mechanism which is capable of high throughput mechanochemical biosensing which uses a DNA origami nanostructure having a plurality of slots into which recognition elements are placed so as to facilitate the detection of an event such as a conformational change in the origami nanostructure, and the apparatus that senses the change.

BACKGROUND OF THE INVENTION

After its discovery in 2006, DNA origami approach has been exploited to fabricate a wide range of 2D and 3D DNA nanostructures. Such nanostructures have been extensively used in many applications including nanorobotics, molecular computation, and drug delivery. However, the biosensing applications of the DNA origami structures have not been explored well. Compared to conventional carbon or metal based substrates for nanoassembly, DNA origami nanostructures provide a biocompatible environment, suitable for many biological reactions. In addition, the chemical components of the origami-based DNA nanostructures are precisely known and can be well controlled at any location, which allow a facile modification and ready incorporation of functional components in the 2D or 3D nanoassembly. These properties render DNA origami an outstanding platform for high throughput and multiplex biosensing.

The present inventors have previously developed a first-in-class biosensing mechanism that employs mechanochemistry principles to detect single-nucleotide polymorphism in DNA sequences. Mechanochemistry is an emerging discipline that deals with the coupling of mechanical and chemical processes. Under mechanical stress, the stability of covalent or non-covalent bonds changes, which either strengthens or weakens molecular structures. In mechanochemical sensing, the binding affinity between a receptor-ligand complex changes mechanical tension of either a free receptor or substrate. To serve as an effective mechanochemical sensor, therefore, the signal transduction unit must exploit mechanical signals, such as mechanical work, tension in a recognition template, or pressure in a system. Since the force signal experiences little environmental interference, the mechanochemical sensor has an advantage of high signal-to-noise ratio. The mechanochemical coupling employed in this type of sensor gives rise to a change in the mechanical property of a template as it recognizes a target through chemical interactions. Therefore, target recognition and signal transduction units in a traditional sensor can be integrated. This not only simplifies the sensing scheme, but also improves the performance of the sensor, since noise present in extra components of a sensing scheme can be avoided.

Due to the superior property of force and spatial resolutions, optical tweezers are an ideal tool used for mechanochemical sensing. However, the throughput of the sensing is low since each time only one template can be investigated. Thus, a problem of the invention was to develop high throughput mechanochemical sensing platforms and sensing methods.

SUMMARY OF THE INVENTION

In accordance with the present invention, a solution to the problem is provided as the inventors have designed and synthesized a DNA origami template to develop high-throughput mechanochemical biosensing in optical tweezers. The origami nanostructure contains multiple slots into which many recognition elements, such as aptamers or DNA strands, can be placed strategically. This modular strategy allows quick and facile switch of different probes without redesigning the whole nanoassembly from scratch.

In a first embodiment, the invention relates to a biosensing platform comprising a multi-tile, e.g. a 7-tile sensing DNA origami nanostructure 10, in which multiple sensing units in the form of recognition elements are placed as the interlocks that connect the adjacent tiles. The binding of a target to any of the recognition element breaks the lock, which generates a change in mechanical signal. The first recognition element was PDGF aptamer which was used as the recognition element in each of the 6 linking elements or "interlocks", labeled 1-6 in FIG. 1a. The invention leads to the detection of 10 pM PDGF within 10 minutes with a detection mode that used a ramping force or a constant force. This represents a significant improvement as 100 pM of a target was previously observed within 30 minutes in the prior art mechanochemical sensing that uses only one sensing unit to demonstrate the capability for sensing of single nucleotide polymorphism. In a further embodiment of the present invention, a simple rewiring of the "interlocks" or staples in the origami design leads to a 3D arrangement of the 7-tile template. This allows the observance of the binding of PDGF and the complementary DNA strand in the same origami. The 3D in tile design also helped with the identification of individual targets by different size change during mechanochemical detection. Thus, the origami sensing of the present invention provides a new paradigm, expanding the limits of self-assembled DNA nanostructures for their applications in the mechanochemical sensing, along with their well-known roles in nanotechnology, drug delivery, and molecular robotics.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1:
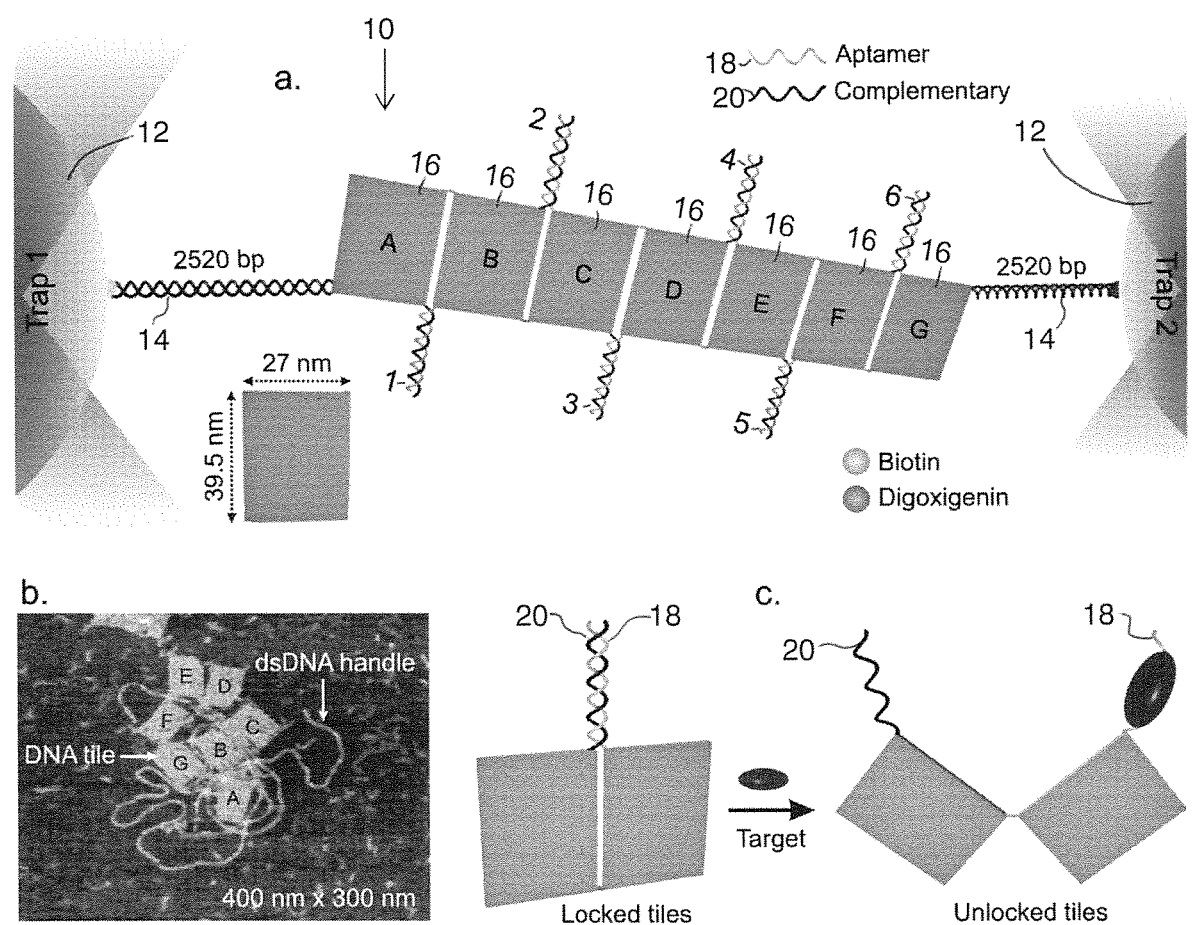
FIG. 1 provides a.) a schematic representation of the experimental set-up for a 7-tile 2D DNA origami nanoassembly tethered between two optically trapped beads through dsDNA handles modified with a terminal digoxigenin or biotin. This figure also includes b.) an AFM image of 7-tile DNA origami nanostructure and c.) illustrates how binding of a target to an aptamer breaks a lock between two adjacent origami tiles.

To prepare a DNA origami structure, a long single-stranded DNA scaffold can be folded into a predesigned 2D or 3D DNA nanostructure aided by short DNA staples. FIG. 1a.-c. illustrates the Experimental set-up for a DNA origami based mechanochemical sensing using optical tweezers (not to scale). A 7-tile 2D DNA origami nanoassembly shown at 10 is tethered between two optically trapped beads 12 through dsDNA handles 14 modified with a terminal digoxigenin or biotin. Each tile 16 of the origami nanostructure has a dimension of 39.5×27 $nm^2$. The adjacent tiles are locked by an aptamer DNA 18 (and its complementary strand 20. FIG. 1b. is an AFM image (400×300 $nm^2$) of the origami nanoassembly depicting 7-tiles and two dsDNA handles. FIG. 1c. is an Illustration of the tile-unlocking due to the target binding to an aptamer lock. Binding of a target, (i.e., the thing being examined such as DNA, RNA or protein), to the aptamer induces the folding of the aptamer, which releases the complementary strand and dissembles the lock. The change in force or bead-to-bead distance due to target induced unlocking of the tiles can be monitored in real time by laser tweezers.

Using this strategy, the present inventors designed and synthesized a 2D DNA origami comprising of seven interlocked tiles by using a linear M13mp18 DNA scaffold (FIG. 1a. and b.). Each tile has a dimension of 39.5×27 $nm^2$. Two adjacent tiles are locked by using complementary DNA strands. One DNA strand contains an aptamer based target recognition element that can change its conformation upon binding with a specific target, thereby unlocking the tiles (FIG. 1c.). By attaching the terminal tiles of the DNA origami to the two optically trapped beads through dsDNA handles, the target binding and the unlocking events in the mechanochemical platform are monitored by optical tweezers (FIG. 1a.).

Figure 2:
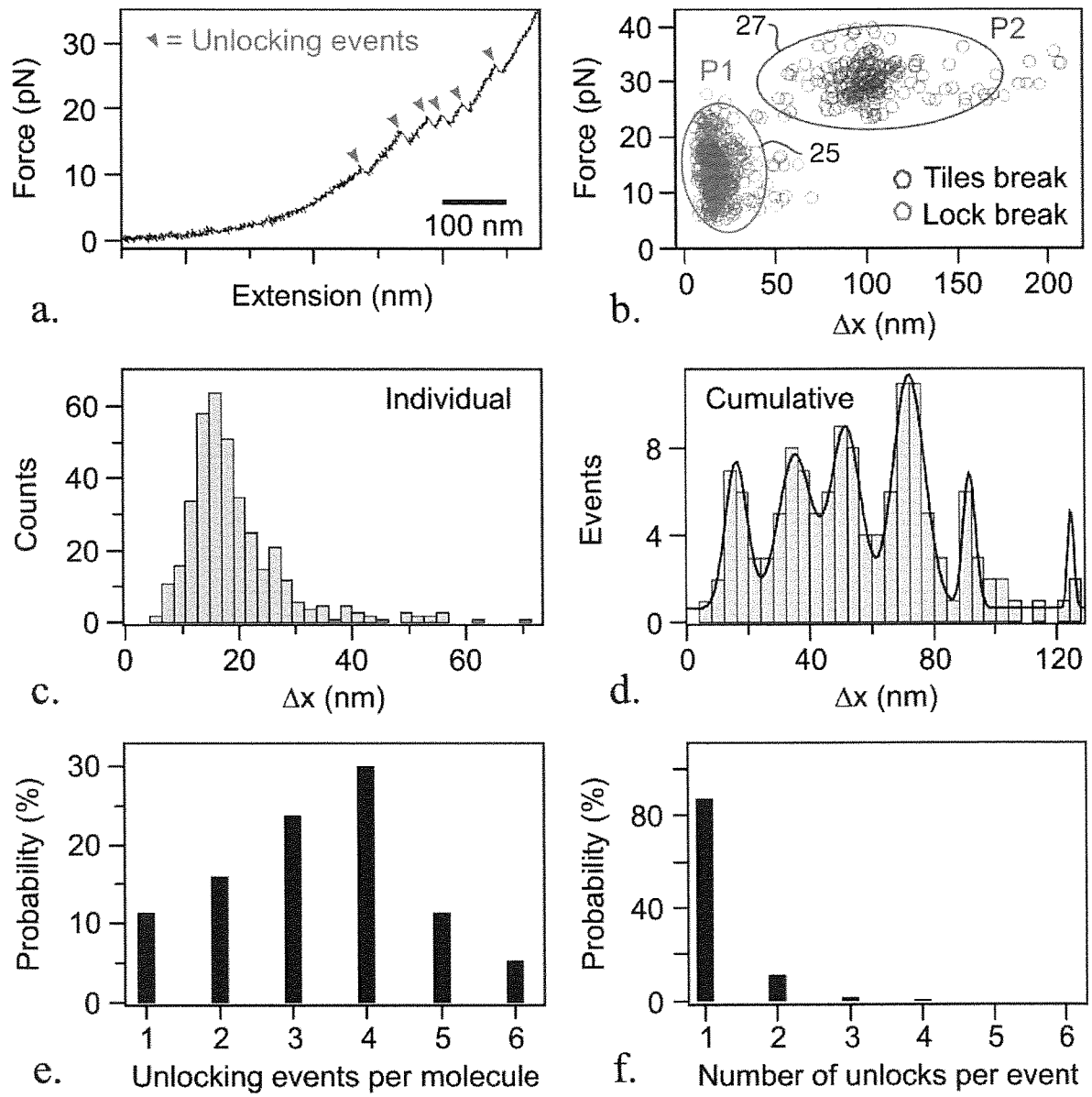
FIG. 2 demonstrates the specific features, mechanochemical properties, of 7-tile DNA origami nanoassembly, illustrating a.) a portion of a typical force-extension curve for the 7-tile nanoassembly, in which the aptamer lock is constituted by a PDGF aptamer and its complementary DNA strand. The force-induced unlocking events are depicted by the arrowheads. b.) the change in extension due to the unlocking or tile disintegration events at a particular force. The ellipses represent 95% confidence interval for each population; c.) histogram of the change in extension for all individual cooperative events; d.) histogram of the cumulative change in extension of all events observed in a single 7-tile nanostructure; e.) probability of unlocking in each nanoassembly shows that 4 unlocking events are most probable; f.) the probability of co-operative unlocking events suggests that one-by-one, rather than simulanteous, unlocking is predominant.

FIG. 2a. shows the mechanochemical properties of the 7-tile nanoassembly, and, in particular, a portion of a typical force-extension curve for the 7-tile nanoassembly in which the aptamer lock is constituted by a PDGF aptamer and its complementary DNA strand. The force-induced unlocking events are depicted by the arrowheads. FIG. 2b. shows the change in extension due to the unlocking 25 or tile disintegration 27 events at a particular force. The ellipses represent 95% confidence interval for each population. FIG. 2c. is a histogram of the change in extension for all individual cooperative events. FIG. 2d. is a histogram of the cumulative change in extension of all events observed in a single 7-tile nanostructure. FIG. 2e. shows probability of unlocking each nanoassembly shows that 4 unlocking events are most probable. FIG. 2f. illustrates the probability of co-operative unlocking events suggests that one-by-one, rather than simultaneous, unlocking is predominant.

Before sensing applications, the present inventors characterized the mechanical properties of this DNA origami structure. Previously, origami has served as tethering handles for mechanical unfolding experiments. However, the mechanical stability of origami has not been well investigated. Force-ramping experiments were performed to increase the tension in the origami nanostructure by moving one of the traps away from the other. This allowed the observation of two types of unfolding events in the force-extension curves. In the force range between 10-25 pN (FIG. 2a.), the inventors observed ≤6 events with a change-in-extension (Δx) of ~15 nm for each transition. This is consistent with the disassembly of the aptamer lock (FIG.

2b., population P1). However, in the range above 30 pN, the inventors observed saw-teeth features with Δx of ~100 nm (FIG. 2b., population P2). In a control construct without any interlocks between adjacent tiles, only ≥30 pN events were observed, confirming that the features between 10-25 pN are associated with the opening of the aptamer interlocks. Such an observation was further validated by performing experiments in which interlocks with shorter dsDNA were used. In these experiments, the unlocking forces (<30 pN) were reduced, which reflects less Watson-Crick base pairing in the dsDNA lock. Based on these results, only the force range between 10-25 pN (FIG. 2b., population P1) was considered for the mechanochemical sensing experiments.

The histogram of the change-in-extension (Δx) for all individual features of population P1 shows a dominant peak at ~15 nm with a shoulder at ~25 nm (FIG. 2c.). However, features with longer (Δx) were rare, suggesting unlocking events were non-cooperative. The histogram for the cumulative (Δx) (FIG. 2d.) demonstrated six peaks with Gaussian centers of 14±0.5, 33±1.0, 50±2.5, 70±2, 90±4, and 123±4 nm, which were consistent with the predicted Δx patterns. The maximum probability of the peak at 70 nm indicates that four tiles, instead of six, are most probable to be locked. This was confirmed by the probability of the unlocked events per molecule based on the observed Δx (FIG. 2e.). The fact that 4 instead of 6 locks were most likely observed reflects the efficiency in the DNA origami preparation in which 100% assembly was rarely observed. The one-by-one, rather than simultaneous, unlocking of the tiles was confirmed in FIG. 2f. in which the most likely transition was associated with a single unlocking event during each unfolding.

Figure 3:
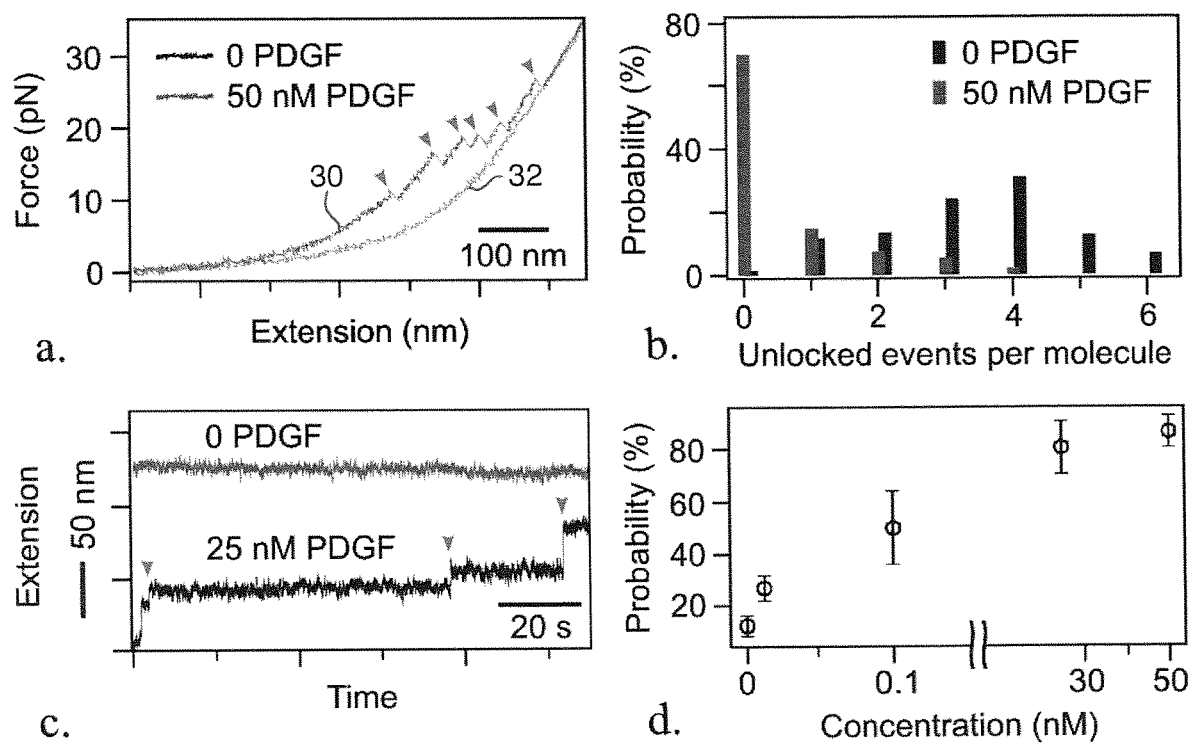
FIG. 3 illustrates the characteristics of 7-tiles DNA origami nanoassembly in the presence of PDGF target. The figure shows a.) representative force-extension curves of the 7-tile DNA nanoassembly in the absence and presence of 50 nM PDGF. In this ramping force detection mode, the force-induced unlocking events were absent in the solution containing the PDGF; b.) comparison of the unlocking events observed per molecule in the absence and presence of the PDGF. The black bars are slightly offset for clarity; c.) real time observation of the target recognition events in the constant force (8 pN) detection mode. Without PDGF, no recognition events were observed. Upon switching to the target solution (24 nM PDGF), the binding of the target unlocked the tiles, leading to the extension jumps; d.) the probability of detecting at least one unlocking event within 10 minutes as a function of the PDGF concentration. Notice that below 0.1 nM the constant force detection was used while ramping force detection was used for higher concentrations.

FIG. 3 illustrates mechanochemical sensing of PDGF using 7-tile nanoassembly in optical tweezers. FIG. 3a. shows representative force-extension curves of the 7-tile DNA nanoassembly in the absence 30 and presence 32 of 50 nM PDGF. In this ramping force detection mode, the force-induced unlocking events (arrowheads) were absent in the solution containing the PDGF. FIG. 3b. shows a comparison of the unlocking events observed per molecule in the absence and presence of the PDGF. The first sets of bars are slightly offset for clarity. FIG. 3c. is a real time observation of the target recognition events in the constant force (8 pN) detection mode. Without PDGF, no recognition events (arrowheads) were observed. Upon switching to the target solution (25 nM PDGF), the binding of the target unlocked the tiles, leading to the extension jumps (arrowheads). FIG. 3d. illustrates the probability of detecting at least one unlocking event within 10 minutes as a function of the PDGF concentration. Below 0.1 nM the constant force detection was used, while ramping force detection was used for higher concentrations.

After characterization of the 7-tile origami nanostructure, the inventors employed this platform to detect the PDGF target. Binding of the PDGF to the aptamer strand in each lock helps to fold and stabilize the secondary structure of the aptamer, which leads to the disassembly of the origami tiles. Indeed, in the presence of 50 nM PDGF, unfolding of origami tiles was not observed as locks had been disintegrated by binding of PDGF prior to the pulling experiments (FIG. 3a.). Analysis of the unlocking events per molecule confirmed this observation. Whereas a maximum of 4 unlocking events per molecule were observed without PDGF, zero unlocking was the most frequent observation with 50 nM PDGF (FIG. 3b.). To detect the binding of PDGF in real time, the inventors switched the detection to the constant force mode, in which the tension in the tethered molecule was maintained at 8 pN while the extension was monitored. As expected, the tension remained constant in a PDGF free solution over time (FIG. 3c.). With 25 nM PDGF, however, many extension jumps were observed (FIG. 3c.). The size of each jump was consistent with expected values when neighboring tiles are separated. In addition, the patterns of the number of jumps were similar to that observed in force ramp mode in FIG. 2e. (data not shown). Using the ramping-force and constant-force detection modes for high (≥25 nM) and low (≤0.1 nM) concentrations of the PDGF, respectively, the inventors performed similar experiments for a series of PDGF concentrations. FIG. 3d. shows the probability of observing at least one unlocking event within 10 minutes. From this diagram, the inventors estimated a detection limit of 10 pM (3σ) within 10 minutes. Compared to the detection limit of 100 pM in 30 minutes in a mechanochemical sensor that contains only one recognition element, the results described here provide a strong support that the multiple recognition probes can effectively improve the detection by lowering the detection limit while significantly reducing the detection time.

Figure 4:
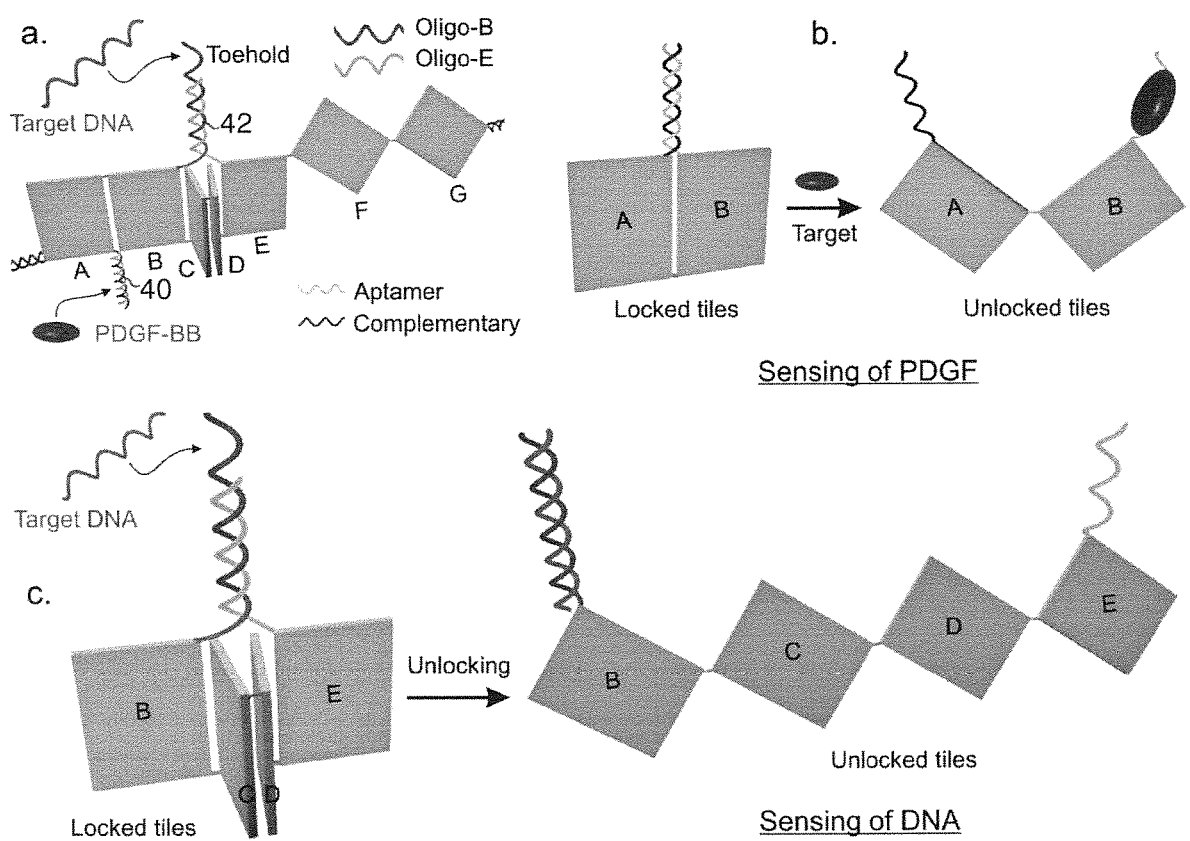
FIG. 4 represents the design of DNA origami construct and the corresponding sensing scheme used in the present invention showing PDGF and Target DNA recognition elements in the same DNA origami nanostructure, specifically illustrating multiplex sensing of the PDGF and Target DNA in a 7-tile DNA origami platform wherein, a.) is a schematic of the DNA construct showing PDGF and Target DNA recognition scheme. The lock between Tiles A and B contains the PDGF recognition element whereas the lock between tile B and tile E contains a DNA sensing element. All other tiles remained unlocked; b.) binding of the PDGF ligand unlocks the tiles A and B causing ~15 nm change in extension; c.) the binding of the Target DNA through a toehold strand displacement mechanism unlocks tiles B, C, D and E, causing ~40 nm change in extension. Because of the twisted geometry of the C and D tiles in the middle, the predicted change in extension would be similar to that of simultaneous disassembly of the locks between B-C, C-D and D-E tiles.

Next, to demonstrate multiplexing capability of our mechanochemical sensing platform, the inventors designed a DNA origami construct comprising of multiple recognition elements (FIG. 4a.). As a proof-of-concept, the inventors incorporated two different probes in the two locks separately. One lock contains the same PDGF aptamer used above while the other consists of a DNA sequence (Oligo-B) to recognize its complementary DNA strand (Target DNA). Oligo-B contains a toehold segment to preferentially bind to the Target DNA over its partially complementary strand (Oligo-E) constituting a lock. To effectively differentiate the binding of each target, the inventors placed the aptamer lock between tiles A and B and the toehold lock comprising of Oligo-B and Oligo-E between tiles B and E (FIG. 4a.) All other tiles were left unconnected to reduce the complexity of the system. Such a design allows extension jumps of ~15 and ~40 nm for the recognition of PDGF by the aptamer lock and Target DNA by the toehold lock, respectively (FIGS. 4b. and c.). Shown in the FIG. 5b. is an AFM image of a typical 7-tile DNA origami in which connection between the tiles B and E are clearly shown, in which the Oligo-B and its partially complementary strand (Oligo-E) were used as a lock. In the presence of the Target DNA, the tiles were disintegrated due to the target DNA binding to the lock.

FIG. 4a.-c. illustrates multiplex sensing of the PDGF and Target DNA in a 7-tile DNA origami platform. FIG. 4a. is a schematic of the DNA construct showing PDGF and Target DNA recognition scheme. The lock 40 between tiles A and B contains the PDGF recognition element whereas the lock 42 between tile B and tile E contains a DNA sensing element. All other tiles were remained unlocked. FIG. 4b. shows binding of the PDGF ligand which unlocks the tiles A and B causing ~15 nm change in extension. FIG. 4c. shows the binding of the Target DNA through a toehold strand displacement mechanism which unlocks tiles B, C, D and E, causing ~40 nm change in extension. Because of the twisted geometry of the C and D tiles in the middle, the predicted change in extension would be similar to that of simultaneous disassembly of the locks between B-C, C-D and D-E tiles.

Figure 5:
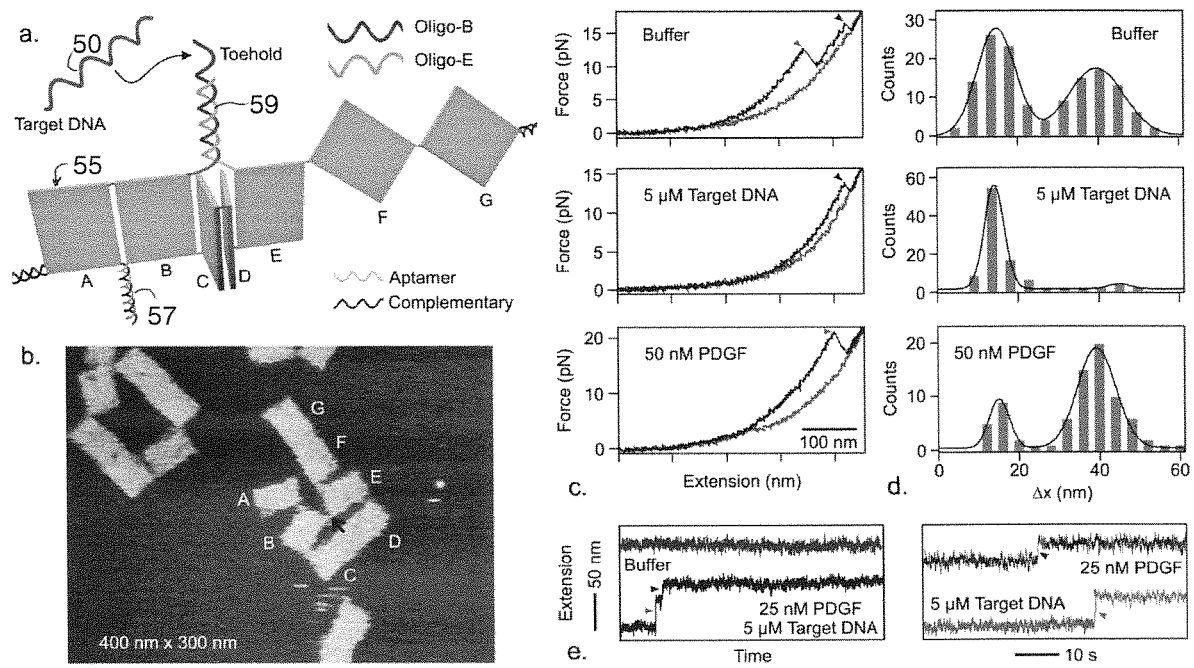
FIG. 5 describes a sensing platform that illustrates simultaneous detection of multiple targets using a 3D DNA origami nanoassembly. The figure includes a.) a schematic of the sending platform. The lock between tiles A and B contains a PDGF aptamer sequence whereas that between the tiles B and E consists of a toehold DNA strand. All other tiles remain unlocked; b.) an AFM image of the construct showing the connection between the tiles B and E. Note that this assembly had no aptamer lock between tiles A and B; c.) typical force-extension curves and d.) corresponding ΔL histograms in target free solution, 5 μm target DNA (middle panel), and 50 nM PDGF (lower panel). In target free solution, two force-induced unlocking events were observed. In the presence of one target, one unlocking even was observed. In the ramping-force detection mode, unlocking events were not observed in the presence of both targets (50 nM PDGF and 5 μM target DNA); e.) real time detection of multiple targets in the constant force mode (8 pN) at low concentrations (25 nM and 5 μM for PDGF and target DNA, respectively). In target free solution, the sensor showed no extension-jumps. When both targets were present, two extension jumps consistent with the breaking of the two locks were observed (left panel). In the solution that contains only one target, one extension jump was observed (right panel).

FIG. 5a.-e. illustrates simultaneous detection of multiple targets 50 using the 7-tile origami nanoassembly 10. FIG. 5a. represents a schematic of the sensing platform 55. The lock 57 between tiles A and B contains a PDGF aptamer sequence whereas the lock 59 between the tiles B and E consists of a toehold DNA strand. All other tiles remained unlocked. FIG. 5b. is an AFM image of the construct showing the connection (black arrow) between the tiles B and E. This assembly had aptamer lock between tiles A and B. FIG. 5c. shows typical force-extension curves and FIG. 5d. shows corresponding ΔL histograms in target free solution (top panel), 5 µM target DNA (middle panel), and 50 nM PDGF (lower panel). In target free solution, two force-induced unlocking events were observed. In the presence of one target, one unlocking event was observed. In the ramping-force detection mode, unlocking events were not observed in the presence of both targets (50 nM PDGF and 5 µM target DNA). FIG. 5e. shows real time detection of multiple targets in the constant force mode (8 pN) at low concentrations (25 nM and 5 µM for PDGF and target DNA, respectively). In target free solution, the sensor showed no extension-jumps. When both targets were present, two extension jumps consistent with the breaking of the two locks were observed (left panel). In the solution that contains only one target, one extension jump was observed (right panel).

With this design, the inventors set out to perform multiplex mechanochemical sensing using ramping-force and constant-force detection modes in optical tweezers. During the ramping-force mode, the F-X curve showed two features in the target free buffer: one has $\Delta x$ of ~40 nm and other with ~15 nm (FIG. 5c. and d., top panel). These two values are consistent with the predicted values for the unlocking of the A-B and B-E tiles, respectively. In the presence of 50 nM PDGF and 5 µM target DNA, such features were absent, suggesting that the binding of the targets to their respective sites prior to the mechanical unfolding experiments.

To confirm these observations, the inventors performed mechanochemical sensing for the two targets separately. In the presence of the target DNA (5 µM) that unlocks the B-E tiles by a toehold mechanism, only the 15 nm feature was observed (FIGS. 5c. and d., middle panel), which corresponded to the force-induced breaking of the A-B tiles. Likewise, in the presence of the PDGF ligand that unlocks the A-B tiles, only the 40 nm feature was observed (FIGS. 4c. and d., bottom panel), which was associated with the unlocking of the B-E tiles.

Further demonstration on the multiplex sensing came from experiments with the constant-force detection. When 8 pN was maintained in the origami template in the target free solution, breaking of the tiles was not observed (FIG. 5e., left panel, upper trace). However, as soon as the sensor was taken to the solution mixture of 25 nM PDGF and 5 µM target DNA, two extension jumps corresponding to the expected breaking of the two locks were observed (FIG. 5e., left panel, lower trace). Such an observation was further verified when sensing was performed against individual targets in which expected extension jump was observed for specific binding event (FIG. 5e., right panel). These findings well established the capability of multiplex sensing in the DNA origami template. With the incorporation of more tiles and the full use of each tile, this mechanochemical sensing strategy is rather flexible to detect many different targets.

In summary, the principle of mechanochemical biosensing using optical tweezers was successfully demonstrated with a 7-tile DNA origami nanoassembly. The incorporation of multiple recognition sites reduces the detection limit as well as the detection time. In addition, it offers a unique and versatile approach for multiplex biosensing. The mechanical signal with little background noise warrants a superior sensitivity of the sensor at the single molecule level. With rapid development of DNA origami techniques, origami structures with increased mechanical stability and more target recognition sites are well within reach after a rational design. Therefore, the new mechanochemical sensing apparatus developed here will expand the limits of self-assembled DNA nanostructures for their potential applications in nanotechnology, drug delivery, and logic gate devices.

While in accordance with the patent statutes the best mode and preferred embodiment have been set forth, the scope of the invention is not limited thereto, but rather by the scope of the attached claims.

What is claimed is:

1. A biosensing platform which is capable of real time, high throughput mechanochemical biosensing, comprising:
    a DNA origami nanostructure, comprising multiple, flat DNA tiles having a plurality of slots between the tiles into which target recognition elements are strategically placed to lock adjacent tiles together, wherein the DNA origami nanostructure is 2-dimensional or 3-dimensional and tethered on terminal ends between two optically trapped beads through dsDNA handles, and
    optical tweezers that sense mechanical signals generated when the target recognition element binds with a target to disassemble the lock and unlock the tiles.

2. The biosensing platform as set forth in claim 1, wherein the DNA origami nanostructure comprises more than 2 and less than 8 tiles, and wherein two or more adjacent tiles are interlocked by the target recognition elements.

3. The biosensing platform as set forth in claim 2, wherein the target recognition elements each comprise an aptamer sequence and a complementary DNA strand.

4. The biosensing platform as set forth in claim 3, wherein the aptamer based target recognition element changes its conformation upon binding with a specific target thereby disassembling the lock and unlocking the tiles.

5. The biosensing platform as set forth in claim 4, wherein the aptamer portion of the target recognition elements comprises Platelet Derived Growth Factor (PDGF) aptamers.

6. The biosensing platform as set forth in claim 5, in which the PDGF aptamer recognizes a target PDGF protein and changes its conformation to unlock the tiles.

7. The biosensing platform as set forth in claim 1, wherein the tiles are approximately flat rectangles, and wherein the tiles have a dimension from 20 to 50 nm by from 15 to 35 nm.

8. The biosensing platform as set forth in claim 7, wherein the DNA origami nanostructure is a 2-dimensional structure having a first end and a second end and is tethered between optically trapped beads by a dsDNA handle at each of the first end and the second end of the DNA origami nanostructure, wherein the dsDNA handles are attached to the first sequential tile and the last sequential tile of the DNA origami nanostructure, and wherein a change in force or bead-to-bead distance due to unlocking of the tiles is monitored in real time by optical tweezers.

9. The biosensing platform as set forth in claim 1, wherein the mechanical signals include a change in a tension or mechanochemical rearrangement of the DNA origami nanostructure due to unlocking of the tiles.

10. The biosensing platform as set forth in claim 1, wherein the lock formed by the target recognition elements opens in response to exposure and binding to a target and the opening occurs at a force between 10-25 pN.

11. The biosensing platform as set forth in claim 10, wherein there are multiple events comprising the opening of the interlocks and the opening events occur one-by-one rather than simultaneous.

12. The biosensing platform as set forth in claim 1, wherein at least two different target recognition elements are used in the same DNA origami nanostructure.

13. The biosensing platform as set forth in claim 2, wherein at least three tiles of the DNA origami nanostructure are interlocked by the target recognition elements.

14. The biosensing platform as set forth in claim 12, wherein the target recognition elements include either a toe-hold DNA segment or a PDGF aptamer, or a combination of both.

15. The biosensing platform as set forth in claim 14, wherein the toe-hold DNA segment recognizes a target DNA sequence and the PDGF aptamer recognizes a PDGF protein and each recognition produces a different mechanical signal upon opening of the lock.

* * * * *